(12) United States Patent
Takama

(10) Patent No.: US 6,423,490 B1
(45) Date of Patent: Jul. 23, 2002

(54) METHOD FOR MEASURING THE CONCENTRATION OF POLYNUCLEOTIDES

(75) Inventor: Toshio Takama, Nara (JP)

(73) Assignee: Kyoto Daiichi Kagaku Co., Ltd., Kyoto (JP)

( * ) Notice: Subject to any disclaimer, the term of this patent is extended or adjusted under 35 U.S.C. 154(b) by 523 days.

(21) Appl. No.: 08/955,727

(22) Filed: Oct. 22, 1997

(30) Foreign Application Priority Data

Oct. 25, 1996 (JP) .............................................. 8-284154

(51) Int. Cl.⁷ ........................... C12Q 1/68; C12P 19/34; C07H 21/02
(52) U.S. Cl. ............................. 435/6; 435/912; 435/94; 536/23.1; 536/24.3; 536/24.31; 536/24.32; 536/24.33
(58) Field of Search ............................. 435/6, 91.2, 94; 536/23.1, 24.3, 24.31, 24.32, 24.23

(56) References Cited

U.S. PATENT DOCUMENTS

| | | | |
|---|---|---|---|
| 4,775,636 A | * 10/1988 | Moeremans et al. | 436/518 |
| 4,781,458 A | 11/1988 | Angel et al. | 356/301 |
| 5,341,215 A | 8/1994 | Seher | 356/445 |
| 5,376,556 A | 12/1994 | Tarcha et al. | 436/525 |
| 5,864,397 A | 1/1999 | Vo-Dinh | 356/301 |
| 5,866,430 A | 2/1999 | Grow | 436/172 |
| 5,869,255 A | 2/1999 | Mathies et al. | 435/6 |
| 5,882,863 A | 3/1999 | Imai et al. | 435/6 |

FOREIGN PATENT DOCUMENTS

| | | |
|---|---|---|
| WO | WO 90/02205 | 3/1990 |

OTHER PUBLICATIONS

Bej et al, "Amplification of nucleic acids by polymerase chain reaction and other methods and their applications", Critical Reviews in Biochem. Mol. Biol. 26(3/4)301–334, 1991.*

Stratagene catalog, p. 39, 1988.*

Graham et al, "Selective detection of deoxyribonucleic acid at ultralow concentration by SERRS", Anal. Chem. 69:4703–4707, Nov. 1997.*

Communication from European Patent Office and attached Search Report (Application No. 97308444 5–2116–), Feb. 1998.

F. Zimmermann et al., "SERRS Study of Acridine Orange and Its Binding to DNA Strands" *J Phys Chem.*, vol. 98, pp. 12796–12804, 1994.

C.H. Munro et al., "Qualitative and Semi–quantitative Trace Analysis of Acidic Monoazo Dyes by Surface Enhanced Resonance Raman Scattering" *Analyst*, vol. 120, pp. 993–1003, Apr. 1995.

Therese M. Cottom et al., "Application of Surface—Enhanced Raman Spectroscopy to Biological Systems" *Journal of Raman Spectroscopy*, vol. 22, pp. 729–742, 1991.

Communication from European Patent Office and attached Search Report (Application No. 97308491.6–2116–), Feb. 1998.

T. Vo–Dinh et al., "Surface–Enhanced Raman Gene Probes" *Anal. Chem.*, vol. 66, No. 20, pp. 3379–3383, Oct. 1994.

A. Helmenstine et al., "Measurement of DNA Adducts Using Surface—Enhanced Raman Spectrocopy" *Journal of Toxicology and Environmental Health*, pp. 195–202, 1993.

K. Kneipp et al., "Surface Enhanced Raman Scattering (SERS) of Nucleic Acids Absorbed on Colloidal Silver Particles" *Journal of Molecular Structure*, pp. 173–179, 1986.

Takahiko Ishiguro, "IM–PCR (Intercalation Monitoring PCR)", *Progress in Medical*, vol. 173, No. 12, pp. 959–963. (English translation of p. 959, Col. 1, lines 1–4 and Figure 1—Homogeneous PCR Assay), 1995.

G. Terrance Walker et al., "Strand Displacement Amplification—an Isothermal, in vitro DNA Amplification Technique", *Nucleic Acids Research*, vol. 20, No. 7, pp. 1691–1696, 1992.

\* cited by examiner

*Primary Examiner*—Jeffrey Fredman
(74) *Attorney, Agent, or Firm*—Merchant & Gould PC

(57) ABSTRACT

A method for measuring the presence of polynucleotide in a sample, comprising the steps of: (1) preparing a sample, an agglutinative agent and an agglutination promoter capable of binding to polynucleotide; (2) mixing said sample, said agent and said promoter; and (3) measuring the degree of agglutination of the agent.

12 Claims, 3 Drawing Sheets not-agglutination | agglutination

METHOD FOR MEASURING THE CONCENTRATION OF POLYNUCLEOTIDES

FIELD OF THE INVENTION

The present invention relates to a method for measuring the concentration of a polynucleotide such as deoxyribonucleic acid (DNA) or ribonucleic acid (RNA) in a sample using agglutination of an agent, and to a kit and apparatus for use in such a method.

BACKGROUND OF THE INVENTION

Recent innovation in the field of genetic engineering has been remarkable. In particular, the development of a polymerase chain reaction (PCR) method has enabled the mass replication of target DNA. The PCR method is based on the principle that DNA polymerase does not function without a primer. The PCR method is used to amplify DNA in large amounts by repeating the following cycle: (1) DNA in a sample is heat denaturated resulting in single stranded DNA; (2) a primer is bonded to the DNA under reduced temperature; and (3) the DNA is formed by thermo-stable DNA polymerase under this condition. Consequently, target DNA can be prepared in large amounts by using a specific primer prepared by chemical synthesis or otherwise. In this method, the replication of target DNA is typically monitored by electrophoresis, a dot blotting method, a PCR-SSCP (Single Strand Conformation Polymorphism) method, a PCR-fluorescence method or the like.

In gene analysis, electrophoresis is a generally used method for detecting the mobility of polynucleotide in a gel in the presence of an electric field. The dot blotting method is used to judge whether or not the amount of analyte has increased or has decreased by the following steps: (1) the polynucleotide extracted from a sample is gradually diluted and the equivalent amount is spotted to a nitrocellulose filter or a nylon film; (2) DNA, RNA and the like labeled by the radioisotope ($^{32}$P) are hybridized with the polynucleotide; and (3) the polynucleotide is exposed to an X-ray film and is analyzed, or the spot portion of film is cut off after hybridization and measured by a scintillation counter. The PCR-SSCP method is a method for detecting the position of a band by autoradiography by the following steps: (1) sample DNA is amplified by the PCR method using the primer labeled by the radioisotope ($^{32}$P); (2) the labeled DNA fragment obtained is heat denaturated resulting in single stranded DNA; and (3) single stranded DNA is separated by electrophoresis using a neutral polyacrylamide gel. The PCR-fluorescence method comprises a first step of obtaining the initial amount of the target nucleic acid by following the change in the fluorescence intensity after PCR has been carried out in the presence of an intercalating fluorescence material (Progress in Medical, Vol. 173, No. 12, Jun. 17, 1995, Pages 959–963).

However, these analytical methods suffer the drawback that special apparatus is needed, the manipulation is complicated and takes a long time. Moreover, the type of polynucleotide which may be analyzed is limited with respect to the chosen analytical method.

More specifically, electrophoresis is a complex and lengthy technique in which it is necessary to prepare a gel as a carrier and to pre-select a gel (size) for which PCR was carried out with regard to the size of DNA. Typically, a sample takes about 75 minutes to electrophorese and it is therefore not a rapid technique.

In the dot blotting method and the PCR-SSCP method, there is normally a safety factor because of the use of a radioisotope. In the method in which no radioisotope is used, the DNA probe must be labeled with a fluorescent substance or a luminescent material. This makes the method complicated and it takes a long time for the manipulation of film transfer. Furthermore, in the PCR-fluorescence method a fluorophotometer is needed and it is difficult to detect single stranded DNA. The conventional analytical methods have in common the problem that the analysis can not be carried out in the presence of materials other than polynucleotide. Therefore, a sample for which PCR has been carried out (a PCR product) should be purified prior to analysis. This makes the overall manipulation lengthy.

It is an object of the present invention to seek to solve these problems and others in the known techniques for measuring polynucleotide concentration in a sample.

SUMMARY OF THE INVENTION

Thus viewed from one aspect the present invention provides a method for measuring the presence of polynucleotide in a sample comprising the steps of: (1) preparing a sample, an agglutinative agent and an agglutination promoter capable of binding to polynucleotide; (2) mixing said sample, said agent and said promoter; and (3) measuring the degree of agglutination of the agent. Preferably the method is used to determine the concentration of said polynucleotide.

The present invention is based on the principle that agglutination of the agent is not promoted by the promoter when the promoter is bound to a polynucleotide. Therefore, by measuring the degree of agglutination, it is possible to confirm the presence of polynucleotide in the sample and in a preferred embodiment to measure its concentration. The measurement of the degree of agglutination may be readily carried out by measuring the absorbance with a spectrophotometer or simply by visual observation. In this invention, mixing the sample with the agent and the promoter is a simple step. Moreover, the method of the invention as a whole may be carried out in a short period of time, since the agglutination of the agent typically occurs in e.g. 1–2 seconds and the measurement of the degree of agglutination may be equally carried out in a short time. Furthermore, the concentration of polynucleotide in a sample may be measured by the method of the invention, even if the materials other than polynucleotide are included in the sample e.g. PCR product that has not been purified.

In the present invention, the expression "an agglutination promoter capable of binding to polynucleotide" refers to material which has the characteristics of bonding to polynucleotide and of promoting the agglutination of the agglutinative agent and which can not promote the agglutination of the agent when bound to polynucleotide. The term "an agglutinative agent" in the present invention refers to material that agglutinates rapidly in the presence of the promoter.

The promoter and the agent may be added to the sample at the same time, or consecutively e.g. the promoter may be added before the agent.

The polynucleotide under investigation may be, for example, single stranded DNA, double stranded DNA, RNA, a complex of RNA and DNA or PNA (Peptide nucleic acid), etc. The method of the present invention is effective on a sample which has been subjected to the PCR method (PCR product) or on a DNA sample. As mentioned above, the PCR method is used for amplifying target DNA. If target DNA is not present in the sample, trace amounts of DNA would be found in the PCR product. Therefore, by measuring the degree of agglutination in accordance with the method of the present invention, it may be determined simply and rapidly whether or not target DNA has been amplified. Further, the amount of amplified DNA can be measured provided a calibration curve relating the degree of agglutination and the amount of DNA has been prepared beforehand.

In addition, the method of the present invention may usefully be applied to samples in which the amplification of DNA is carried out by the Strand displacement amplification method (SDA method) or by the Ligase chain reaction (LCR method) and in which the amplification of RNA is carried out using the Qβ replicase (Qβ method). The SDA method includes the method described in Nucleic Acids Research, Vol.20. No.7 1691–1696. The LCR method is that method in which thermo-stable DNA ligase which is not denaturated by heat (even at 94° C.) is used. This method is based on the principle that for normal DNA samples having no mismatches, the two kinds of oligonucleotide used are bonded by the DNA ligase, resulting in them functioning as a substrate in the next reaction cycle and DNA amplification. Where the DNA sample has mismatches, the reaction stops, since the two kinds of oligonucleotide are not able to bond.

A RNA replicase which has high specificity to substrate RNA is used in the Qβ method. Firstly, the plasmid vector connected to MDV-1-RNA (RNA changing to DNA) is placed downstream of the promoter of T7 RNA polymerase and the DNA fragment to be amplified is inserted into the MDV-1 (the fragment of about 20–800bp can be inserted into it). After it is cut by using a restriction enzyme, the DNA fragment is charged to RNA by using T7 RNA polymerase. The MDV-1-RNA in which the DNA fragment is inserted can be amplified by repeating the replicative cycle with Qβ replicase.

In addition, the method of the present invention may usefully be applied to samples in which the amplification of DNA or RNA is carried out by a 3SR method, a NASBA method, a CPR method, a SIR method or the like. The NASBA method is an RNA replication method and the other methods are DNA replication methods.

For measuring the concentration of double stranded DNA (including a sample treated by a DNA replication method) in accordance with the invention, the agent may be 4',6-diamidino-2-phenylindole (DAPI) which is shown in formula 1 below, ethidium bromide (EtBr), thiazole orange, bisbenzimide (Hoechst 33258, product of Hoechst AG) which is shown in formula 2 below and acridine orange. In addition, SYBR Green I (Molecular Probes Co., Ltd.) may be included. It is preferable that the chosen agent is DAPI, since it bonds to double stranded DNA to form a complex but barely bonds to other material such as RNA. Therefore, double stranded DNA can be selectively detected by DAPI.

<Formula 1>

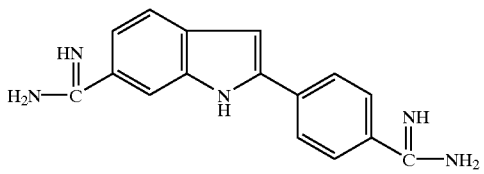

<Formula 2>

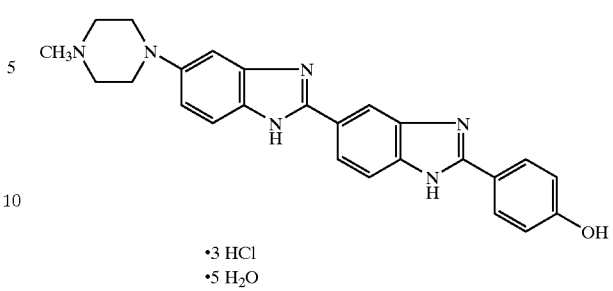

·3 HCl
·5 H₂O

For measuring the concentration of RNA (including RNA amplifying sample) in accordance with the invention, the promoter may be e.g. EtBr, thiazole orange, bisbenzimide (Hoechst 33258, product of Hoechst AG) which is shown in formula 2 and acridine orange. Additionally, SYBR Green II (Molecular Probes Co., Ltd.) may be included. Among the materials mentioned above, SYBR Green II bonds to RNA more selectively to form a complex.

For measuring the concentration of single stranded DNA in accordance with the invention SYBR Green II may be used as the promoter.

For measuring the concentration of a complex of RNA and DNA an agent which bonds to DNA and/or RNA may be used as the promoter In the present invention, the agent may be, for example, a silver colloid, a gold colloid, a copper colloid, or a latex which may be simply manufactured and easily treated. The latex may be, for example, a coloured latex, a carboxylated latex or an aminated latex. A commercial product may be used as the silver colloid and the like in the method of the invention. The silver colloid and the like may be prepared in a conventional manner.

In the measuring step, it is preferably to measure the degree of agglutination by straightforward visual observation. If it is desired to measure the concentration of polynucleotide, it is preferable to determine the degree of agglutination by measuring the absorbance with a spectrophotometer thereby enabling accurate measurement.

Viewed from a further aspect the present invention provides a kit comprising a reagent R1 comprising an agglutination promoter capable of bonding to polynucleotide and a reagent R2 comprising an agglutinative agent. The measurement of the concentration of polynucleotide may be carried out more rapidly and easily by using this kit.

Viewed from a yet further aspect the present invention provides an apparatus comprising: (1) means for introducing a reagent R1 comprising an agglutination promoter capable of bonding to polynucleotide into a sample; (2) means for introducing a reagent R2 comprising an agglutinative agent into the mixture produced in step (1); and (3) a system for measuring the absorbance of radiation by the agglutination. This apparatus enables the measurement of the concentration of polynucleotide to be carried out automatically.

DETAILED DESCRIPTION OF THE INVENTION

Figure 1:
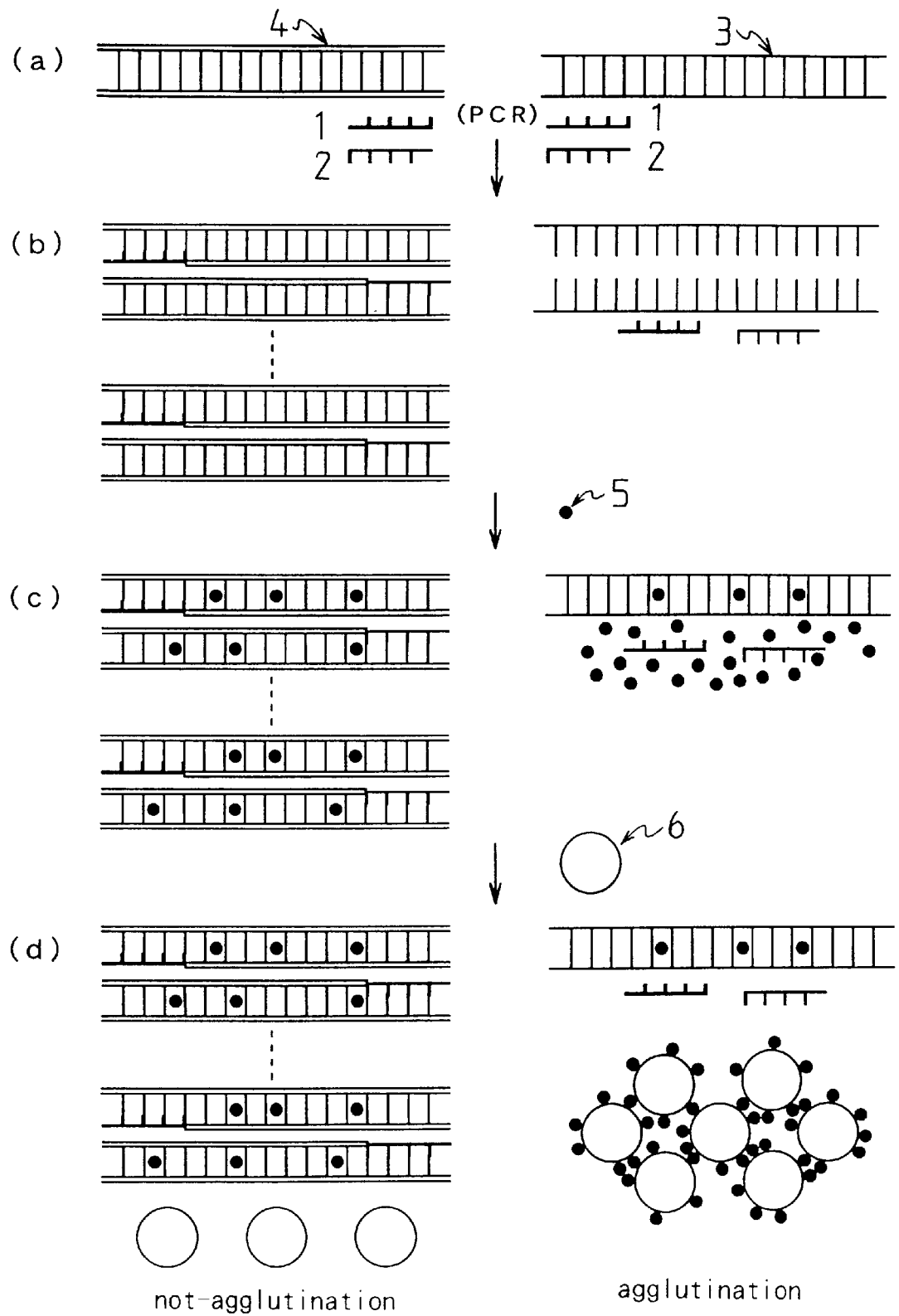
FIG. 1 shows a series of manipulations in an embodiment in which the method of the present invention was applied to the PCR.

FIG. 1 shows an example in which the present invention has been applied to a sample upon which PCR has been carried out. In the example on the right side of FIG. 1, PCR has been carried out for samples in which target DNA (3) is not present, and on the left side, PCR has been carried out for samples in which target DNA (4) is present.

As shown in Figure (a), a DNA sample is prepared initially. Primers (1) and (2), DNA polymerase (not shown in this Figure) and deoxyribonucleotidetriphosphate (dNTP, not shown in this Figure) are added to the samples. When the sample is heated, DNA is denatured and dissociated to single stranded DNA. When the sample is cooled, the primers 1 and 2 are bonded to the target DNA complementally but not to DNA other than target DNA. As shown in Figure (b), extension occurs in the target DNA by the DNA polymerase. However, it does not occur in DNA other than the target DNA, since the primers have not been bonded to the DNA. When a series of manipulations are repeated about 20–30 times, the target DNA is amplified in large amounts as shown in Figure (b). On the other hand, DNA other than target DNA is not amplified at all.

As shown in Figure (c), when the promoter (5) is added to the samples, it is intercalated into double stranded DNA. Consequently, there is a lot of double stranded DNA in the target DNA sample as shown in the Figure, and almost all the promoter is bonded to the double stranded DNA. On the other hand, in the sample not comprising target DNA, the greater part of the promoter is present in the sample in free state, since there is almost no double stranded DNA. A silver colloid (b) acting as an agglutinative agent is added to the samples as shown in Figure (d). If the promoter is bonded to DNA in the target DNA sample as shown in the Figure, silver colloid observed through the naked eye may be ignored as being in trace amounts. On the other hand, if the promoter is present in free state in the sample, the agglutination of the silver colloid is enhanced and agglutination may be easily detected by visual observation through the naked eye.

Consequently, it may be determined that target DNA is not present in the sample in which agglutination of the silver colloid is observed, and that target DNA is present in a sample in which agglutination of silver colloid is not observed or is observed in trace amounts. Thus, according to the present invention, polynucleotide analysis may be easily carried out in a short time without using any special apparatus such as in conventional electrophoresis.

In the method of the invention, promoter (a) and agglutinative agent (b) are normally added in the volume ratio a:b=1:9, although the precise ration is determined according to the type of polynucleotide under investigation.

In the method of the invention, when the measurement of the degree of agglutination is carried out by measuring absorbance using a spectrophotometer, the absorbance wavelength is determined by the identity of the agglutinative agent. For example, the absorbance of silver colloid is 390 nm and gold colloid is 520 nm.

In the kit according to the present invention the reagent R1 may include materials other than the promoter e.g. stabilizers such as polyphosphoric acid, polyvinyl alcohol (PVA), polyvinyl-pyrrolidone (PVP), surfactant and the like.

The kit may be used in accordance with the method of the invention described above, i.e. the reagents R1 and R2 are consecutively added to the sample, mixed together, and the degree of agglutination of the agglutinative reagent in the sample is measured. The kit enables the measurement of the concentration of polynucleotide to be carried out rapidly and easily, since the proper amount of the necessary components have been prepared beforehand and thus it is not necessary to prepare the reagents each time the measurement is carried out as in conventional methods.

Figure 2:
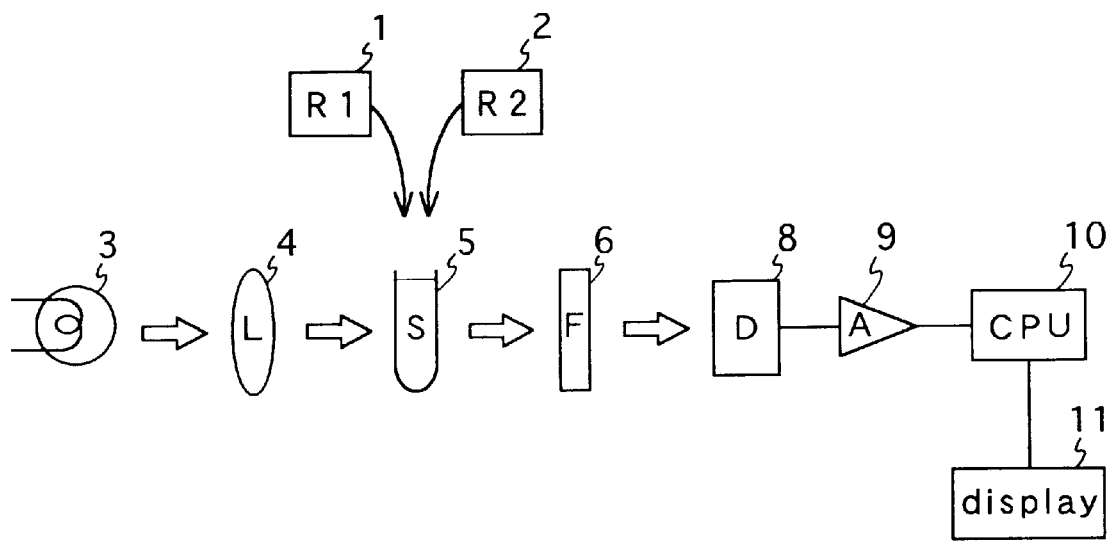
FIG. 2 is a schematic diagram showing one embodiment of the apparatus according to the present invention.

FIG. 2 shows one example of an apparatus according to the present invention. The apparatus is provided with supply means 1 for the reagent R1, supply means 2 for the reagent R2 and a system for optical measurement. The supply means 1 and 2 normally comprise a pump, a stepping motor (or a DC motor), a syringe, etc. and are able to control the supply sequence so that reagent R1 is supplied to the sample before reagent R2. The measurement device comprises a light source 3, a lens 4, a filter 6, a detector 8, a signal amplifier 9, a computer (a central processing unit) 10 and a display 11. The cell 5 into which the sample is injected is placed between the lens 4 and the filter 6.

In this apparatus the measurement of the concentration of polynucleotide is carried out as follows. Firstly, the reagents R1 and R2 are introduced consecutively into the cell 5 in which the sample has been injected by supply means 1 and 2. Radiation from source 3 with a specific wavelength passes through the lens 4, the cell 5 and the filter 6 in order and reaches the detector 8. The intensity of the light is transformed into an electrical signal by the detector 8 and the electrical signal is amplified by the signal amplifier 9. Arithmetic processing is carried out by the computer 10 and the result of the arithmetic processing is indicated on the display 11.

Figure 3:
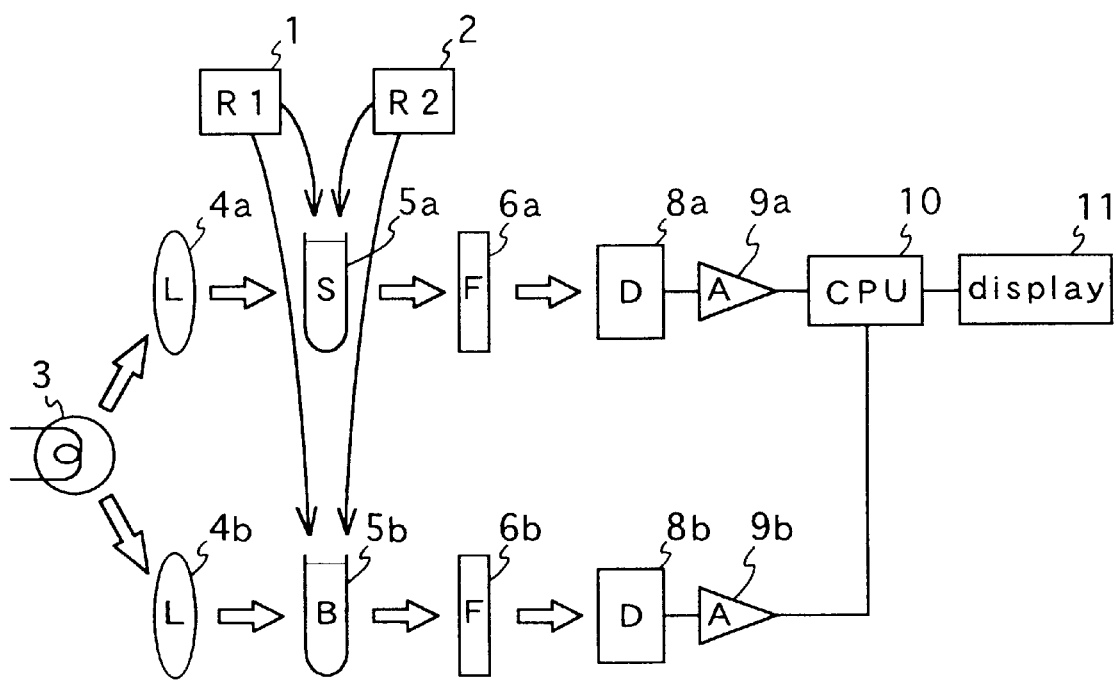
FIG. 3 is a schematic diagram showing another embodiment of the apparatus according to the present invention.

FIG. 3 shows another embodiment of the apparatus according to the present invention. The apparatus shown in this Figure is an apparatus measuring difference spectra. The basic construction is identical with the apparatus in FIG. 2 and the same parts in both FIGS. 1 and 2 are identified by the same number.

The apparatus is provided with an absorbance measuring device and the system measuring blank. First, the reagents R1 and R2 are introduced respectively by the supply means 1 and 2 into the cell 5a into which sample has been injected, and the cell 5b into which purified water or buffer solution has been injected. Next, the irradiated light from light source 3 with the specific wavelength passes through the lenses 4a and 4b, the cells 5a and 5b, and the filters 6a and 6b in order and reaches the detectors 8a and 8b respectively. The intensity of transmitted light in the sample and the blank is transformed into an electrical signal by detectors 8a and 8b, and then the electrical signal is amplified by the signal amplifiers 9a and 9b and transferred to the computer 10. The arithmetic processing of the electrical signal is carried out by the computer 10 and the intensity of the transmitted light from the blank is deducted form the intensity of the transmitted light of the sample. The result is indicated on the display 11. In this way, the effect of absorption by other materials can be eliminated by the difference spectra thereby allowing a more accurate result to be obtained.

In the above description, the polynucleotide is double stranded DNA amplified by PCR. However, the present invention should not be limited to the example. The present invention may be equally applied to double stranded DNA amplified by the SDA method or by the LCR method, to RNA, to RNA amplified by the Qβ method, to single stranded DNA or to a complex of RNA and DNA. The same steps as mentioned above may be carried out using a promoter selected according to the kind of polynucleotide to be analyzed, allowing the concentration of polynucleotide such as RNA to be determined rapidly and easily.

The following examples are intended to illustrate the invention in a non-limiting manner:
Embodiment

EXAMPLE A

First, a PCR buffer was prepared by dissolving the reagents shown below into purified water (1 l).

| (The PCR Buffer Composition) | |
|---|---|
| Tris-HCl (pH 8.3) | 100 mM |
| KCl | 500 mM |
| MgCl$_2$ | 15 mM |

The PCR reaction solution was prepared by adding the materials shown below to 10 μl of the PCR buffer. The primers 1 and 2 shown below are designed so that part of 6012 base pair (bp) of the following λ DNA is amplified.
(Mixed Materials)
 dNTP (dATP, dCTP, dGTP, dTTP, 2.5 mM): 8 μl
 primer 1 (20 pmol/μl): 1 μl
  Sequence: 5'-GATGAGTTCGTGTCCGTACAACT-3'
 primer 2 (20 pmol/μl): 1 μl
  Sequence: 5'-CCACATCCATACCGGGTTTCAC-3'
 TaqDNA polymerase (50 U/μl): 0.5 μl
 DNA (λ DNA, 1 μg/ml): 1 μl
 distilled water: 78.5 μl
Using this PCR reaction solution, PCR was carried out by the following cycle.
(PCR Cycle)
 Step a (94° C., 10 minutes): 1 cycle
 Step b (94° C., 1 minute) → Step c (68° C., 4 minutes): 30 cycles
 Step d (68° C., 7 minutes): 1 cycle
DNA purification was carried out, i.e. first, the PCR product was electrophoresed using an agarose-gel (150 mA, 2 hours) whereby the target DNA fraction was separated out. The gel portion having the band of the target DNA was cut and ejected. The gel was put into a dialysis tube with Tris-Acetate (TAE) buffer and both ends of the tube were closed with sealers. The dialysis tube was installed in the electrophoresis bath so that the major axis of the dialysis tube was at right angles to the direction of the electric field. The bath was filled with TAE buffer and energized (150 mA, 3 hours). After energizing, the TAE buffer recovered from the dialysis tube was transferred to a centrifuging tube and precipitation was carried out with ethanol. The precipitate was dissolved in distilled water. The solution was purified DNA sample.

Next, 10 μl DAPI aqueous solution (concentration: $10^{-4}$ mol/l) was mixed with 40 μl of the DNA sample. 360 μl silver colloid aqueous solution (concentration: 0.17 mg/ml) was mixed with the mixture solution to prepare the test sample. In the test sample, the degree of agglutination was measured by observation through the naked eye and by measurement of absorbance (390 nm) using a spectrophotometer. The result is shown in Table 1.

As a control, PCR and the purification were carried out in the same manner as above but using 1 μl distilled water instead of DNA solution. After DAPI and a silver colloid were added, the degree of agglutination was measured as above. The result is shown in Table 1.

TABLE 1

| | PCR(Positive) | PCR(Negative) |
|---|---|---|
| Agglutination Appearanee | not agglutinate (+) (yellow or brown) | agglutinate(−) (gray precipitate) |
| Absorbance at 390 nm | 0.9 | 0.03 |

As shown in Table 1, a difference in appearance and in the measured absorbance was clearly found between the case where the part of 6012 (bp) of λ-DNA was amplified by PCR and the case where the part of 6012 (bp) of λ-DNA was not amplified (the control). From these results, it may be seen that the method according to the present invention may be used to judge rapidly and easily whether or not DNA has been replicated by the PCR method.

EXAMPLE B

5 μl DAPI solution (concentration: $10^{-4}$M) was added to 40 μl λ–DNA(48502 bp) (concentration: 8OD) followed by 360 μl silver colloid. The degree of agglutination was measured in the same manner as in Example A. The result is shown in Table 2.

As a control, 5 μl DAPI solution (concentration: $10^{-4}$M) was added to 40 μl purified water and then 360 μl silver colloid was added. The degree of agglutination was measured in the same manner as in Example A. The result is shown in Table 2.

TABLE 2

| | Presence of λ-DNA | Absence of λ-DNA |
|---|---|---|
| Agglutination Appearance | not agglutinate(+) (yellow or brown) | agglutinate(−) (gray precipitate) |
| Absorbance at 390 nm | 1.2 | 0.03 |

As shown in Table 2, a difference in appearance and in the measured absorbance was clearly found between the case where λ-DNA was present and the case where λ-DNA was not present (the control).

EXAMPLE C

Single stranded oligo DNA (Toua Synthetic Chemistry Corporation, the base number: 30 mer) was prepared, whose base sequence is

5'-CCCCCTAGCTTGGCAATGTACATGACAAGT-3'.

As a next step, 10 μl DAPI solution (concentration: $10^{-4}$M) was added to 30 μl of the oligo DNA (concentration: 10OD) and then 360 μl silver colloid was added. The degree of agglutination was measured in the same manner as in Example A. The result is shown in Table 3.

As a control, 10 μl DAPI solution (concentration: $10^{-4}$M) was added to 30 μl purified water and then 360 μl silver colloid was added. The degree of agglutination was measured in the same manner as in Example A. The result is shown in Table 3.

TABLE 3

|  | Presence of oligo DNA | Absence of oligo DNA |
| --- | --- | --- |
| Agglutination Appearance | not agglutinate(+) (yellow or brown) | agglutinate(−) (gray precipitate) |
| Absorbance at 390 nm | 1.1 | 0.03 |

As shown in Table 3, a difference in appearance and in the measured absorbance was clearly found between the case where single stranded oligo DNA was present and the case where single stranded oligo DNA was not present (the control). These results demonstrate that, by using the method according to the present invention, it is possible to judge rapidly and easily whether or not single stranded oligo DNA is present.

EXAMPLE D

5 μl DAPI solution (concentration: $10^{-4}$M) was added to 40 μl λ-DNA(48502 bp) (concentration: 8OD) and then 360 μl gold colloid was added. The degree of agglutination was measured in the same manner as in Example A. The result is shown in Table 4.

As a control, 5 μl DAPI solution (concentration: $10^{-4}$M) was added to 40 μl purified water and then 360 μl gold colloid was added. The degree of agglutination was measured in the same manner as in Example A. The result is shown in Table 4.

TABLE 4

|  | Presence of λ-DNA | Absence of λ-DNA |
| --- | --- | --- |
| Agglutination Appearance | not agglutinate(+) wine color | agglutinate(−) gray |
| Absorbance at 520 nm | 1.4 | 0.3 |

As shown in Table 4, a difference in appearance and in the measured absorbance was clearly found between the case where λ-DNA was present and the case where λ-DNA was not present (the control).

EXAMPLE E

PCR was carried out in the same manner as in Example A, thereby obtaining PCR product. The degree of agglutination in the PCR product was measured in the same manner as in Example A without purifying the DNA. The result is shown in Table 5.

As a control, PCR was carried out in the same manner as above but using 1 μl distilled water instead of DNA solution. Further, the degree of agglutination was measured in the same manner as above. The result is also shown in Table 5.

TABLE 5

|  | PCR(Positive) | PCR(Negative) |
| --- | --- | --- |
| Agglutination Appearance | not agglutinate(+) yellow | agglutinate(−) brown |
| Absorbance at 390 nm | 1.2 | 0.5 |

As shown in Table 5, a difference in appearance and in the measured absorbance was clearly found between the case where the part of 6012 (bp) of λ-DNA was amplified by PCR and the case where the part of 6012 (bp) of λ-DNA was not amplified (the control). These results demonstrate that, by using the method according to the present invention, it is possible to judge rapidly and easily whether or not DNA has been replicated even in a PCR product which has not been purified.

EXAMPLE F

10 μl DAPI solution (concentration: $10^{-4}$M) was added to 80 μl λ-DNA(48502 bp) having various concentrations (33.5 mg/ml, 27 mg/ml, 16.75 mg/ml, 3.35 mg/ml) and then 720 μl silver colloid was added. The absorbance at 390 nm was measured and the relationship between the DNA concentration and the absorbance was studied. The result is shown in FIG. 4.

Figure 4:
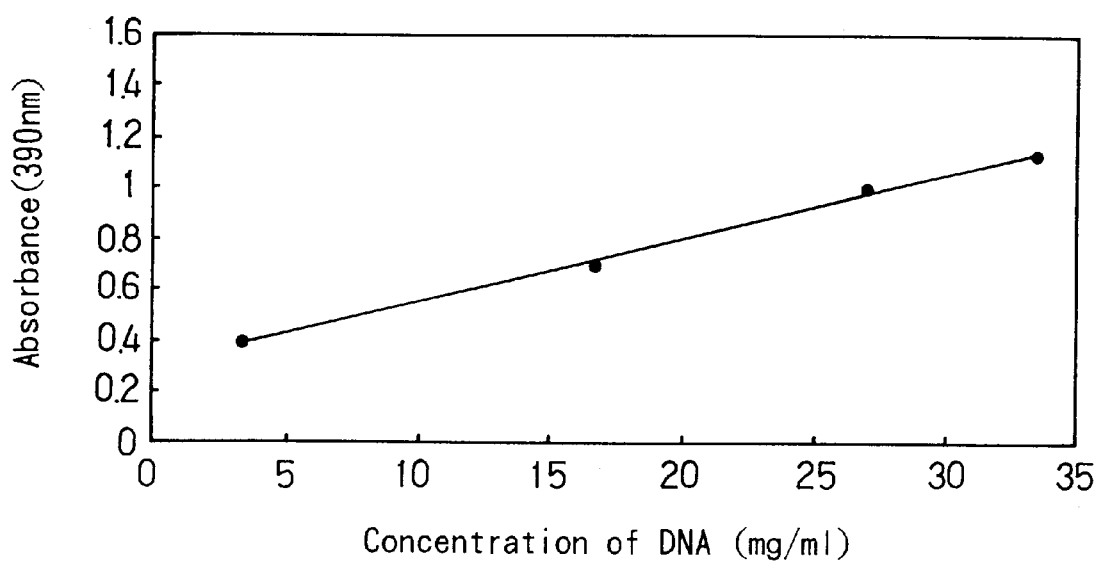
FIG. 4 is a graph showing the relationship between DNA concentration and absorbance in one embodiment of the present invention.

FIG. 4 shows that as the DNA concentration was increased the absorbance increased linearly. This graph may be used as a calibration curve and the calibration curve may be used to measure the DNA concentration in an unknown sample.

The invention may be embodied in other specific forms without departing from the spirit or essential characteristics thereof The embodiments disclosed in this application are to be considered in all respects as illustrative and not restrictive, the scope of the invention being indicated by the appended claims rather than be the foregoing description, and all changes which come within the meaning and range of equivalency of the claims are intended to be embraced therein.

What is claimed is:

1. A method for determining whether a target polynucleotide in a sample subjected to polynucleotide amplifying has been amplified, comprising the steps of:
    (a) adding to the sample an agglutinative agent and an agglutination promoter capable capable of binding to polynucleotide;
    (b) detecting the agglutination of the agglutinative agent; and
    (c) determining on the basis of the agglutination whether the target polynucleotide in the sample has been amplified.

2. A method as claimed in claim 1, wherein the polynucleotide is double stranded deoxyribonucleic acid (DNA).

3. A method as claimed in claim 2, wherein the sample is one or more of the samples selected from the group consisting of a sample treated by the polymerase chain reaction (PCR) method, a sample treated by the Strand displacement amplification (SDA) method and a sample treated by Ligase chain reaction (LCR) method.

4. A method as claimed in claim 1, wherein the polynucleotide is ribonucleic acid (RNA).

5. A method as claimed in claim 4, wherein the sample is treated by the Qβ method with Qβ-replicase.

6. A method as claimed in claim 1, wherein the polynucleotide is single stranded DNA.

7. A method as claimed in claim 1, wherein the polynucleotide is a complex of RNA and DNA.

8. A method as claimed in claim 1, wherein said promoter is one or more of the promoters selected from the group consisting of 4',6- diamidino-2- phenylindole, ethidium bromide, bisbenzimide and acridine orange.

9. A method as claimed in claim 1, wherein said promoter is one or more of the promoters selected from the group consisting of ethidium bromide, thiazole orange, bisbenzimide and acridine orange.

10. A method as claimed in claim 1, wherein said agent is one or more of the agents selected from the group consisting of a silver colloid, a gold colloid, a copper colloid and a latex.

11. A method as claimed in claim 1, wherein step (b) is carried out by visual observation.

12. A method as claimed in claim 1, wherein step (b) is carried out by measuring the absorbance of radiation using a spectrophotometer.

* * * * *